(12) United States Patent
Doran et al.

(10) Patent No.: US 7,633,048 B2
(45) Date of Patent: Dec. 15, 2009

(54) FAST LASER SCANNING OPTICAL CT APPARATUS

(76) Inventors: Simon John Doran, 13 Hedgeway, Guildford (GB) GU27RB; Nikola Krstajic, 18 Bromgrove Road, Flat 2, Sheffield (GB) S102LR (*) Notice: Subject to any disclaimer, the term of this patent is extended or adjusted under 35 U.S.C. 154(b) by 0 days.

(21) Appl. No.: 12/148,272

(22) Filed: Apr. 17, 2008

(65) Prior Publication Data

US 2008/0277567 A1    Nov. 13, 2008

Related U.S. Application Data

(60) Provisional application No. 60/925,178, filed on Apr. 19, 2007.

(51) Int. Cl.
*G06M 7/00* (2006.01)
*G01N 15/06* (2006.01)
*G01J 4/00* (2006.01)
*G01B 11/30* (2006.01)

(52) U.S. Cl. ............... 250/221; 250/577; 356/369; 356/607

(58) Field of Classification Search ... 250/201.1–201.4, 250/216, 221, 275–577; 356/367–370, 602–610
See application file for complete search history.

(56) References Cited

U.S. PATENT DOCUMENTS

| | | | | |
|---|---|---|---|---|
| 5,257,092 A | * | 10/1993 | Noguchi et al. | 356/367 |
| 6,483,584 B1 | * | 11/2002 | Lee et al. | 356/369 |
| 7,304,315 B2 | * | 12/2007 | Iketaki et al. | 250/461.2 |

* cited by examiner

*Primary Examiner*—Georgia Y Epps
*Assistant Examiner*—Don Williams
(74) *Attorney, Agent, or Firm*—Richard D. Wood

(57) ABSTRACT

Disclosed are scanning devices which measure and quantify optical properties within an object such as the absorption of light, refractive index, light scattering, fluorescence, and phosphorescence. Through the use of two rotating plane mirrors and two paraboloid mirrors, a laser light beam is made to traverse the object to be scanned wherein the beam is always parallel to the optical axis. The invention provides an improvement over previously reported scanning devices by virtue of increased speed and resolution. Two-dimensional projections gleaned by each scan of the object are reconstructed into a three-dimensional image through the use of various computer techniques.

13 Claims, 7 Drawing Sheets

FAST LASER SCANNING OPTICAL CT APPARATUS

CROSS-REFERENCES TO RELATED APPLICATIONS

This application claims the benefit of U.S. Provisional Application Ser. No. 60/925,178, filed Apr. 19, 2007.

STATEMENT REGARDING FEDERALLY SPONSORED RESEARCH OR DEVELOPMENT

Not Applicable.

REFERENCE TO A SEQUENCE LISTING

Not Applicable.

FIELD OF THE INVENTION

The invention relates to an optical scanning apparatus which measures the three-dimensional distribution of optical properties within the volume of an object.

BACKGROUND OF THE INVENTION

The invention provides a device which makes non-invasive, quantitative, and precise measurements of optical properties across the three-dimensional volume of objects which transmit light. The invention is within the general field of optical computed tomography (optical CT). The invention is directed to devices which measure and quantify optical properties which include, but are not limited to, absorption of visible light, absorption of ultraviolet light, absorption of infrared light, refractive index, light scattering, fluorescence, phosphorescence, and combinations of these. One application of the invention is to quantify the three-dimensional distribution of a radiation dose absorbed by an object in which optical properties of the object have been made to change predictably with the interaction with ionizing radiation. This application allows the planning and execution of a radiotherapy treatment to be simulated, measured, and evaluated on an inanimate object before applying it to humans and is particularly important for validating complex radiotherapy treatment plans. Without such an experimental measurement, it is impossible to be sure that the dose received by a patient is that claimed by the treatment planning software. In this application, the invention provides information by measuring the optical density of the sample at all points in the three-dimensional volume. The object is specially designed so that its optical properties (in particular, its absorption or scattering coefficients at the wavelength of operation of the system) change with the absorption of radiation in a predictable and quantitative manner. A full review of the history and principles of optical CT scanning in radiotherapy dosimetry was presented (S J Doran and N Krstajić, *J. Phys. Conf. Ser.* 56 (2006) 45-57).

Optical CT has been utilized to produce computer-rendered images of various structures which permit the transmission of incident light. Optical CT allows the generation of three-dimensional images through tomographic reconstruction of a stepped series of two-dimensional data arrays ("slices"). Various techniques have been devised for the imaging of structures of various sizes, ranging from small (less than 1 mm field-of-view) to large (for example, a transparent cylinder having a radius of 10 cm).

One field in which optical CT has made an impact is the evaluation of the difference in optical properties within a three-dimensional translucent or transparent object. Three-dimensional dosimeters have been provided in which certain optical properties within the dosimeter volume change predictably upon interaction with ionizing radiation. These optical properties include degree of light scattering, absorbance, refractive index, and combinations of these. These three-dimensional dosimeters have found use in the evaluation of complex radiotherapy treatment plans such as Intensity-Modulated Radiation Therapy (IMRT) and three-dimensional conformal radiotherapy (3DCRT). In order to be useful, these three-dimensional dosimeters must be scanned to evaluate the optical data contained within. Optical CT scanners have been developed to meet this need. The Optical CT scanners all store in computer memory a series of two-dimensional images which are transformed by various algorithms and reconstructed into three-dimensional images by a computer program.

An Optical CT laser scanner for three dimensional dosimetry has been described (Gore et al, 1996, *Physics in Medicine and Biology* 41 2695-2704; U.S. Pat. No. 6,218,673 to Gore et al). The device disclosed employs a laser light source which is made to scan through a cylindrical dosimeter. The incident laser beam is reflected through 90 degrees by a first mirror and passed through the dosimeter contained within a water bath. The transmitted beam is reflected through 90 degrees by a second into a detector. A two-dimensional slice is produced by moving the first and second mirrors simultaneously along a carriage in a plane parallel to the optical axis. The dosimeter is rotated through a small angle in a plane orthogonal to the optical axis and another scan is measured. This scan and rotate process is repeated until the dosimeter has been rotated through 180 degrees. The entire volume of the dosimeter can only be scanned by employing a series of stepped rotations and axial translation of the dosimeter. Thus, after a large number of scans and stepped rotations of the dosimeter (180 scans when the step angle is set to 1 degree), the dosimeter must be indexed axially (e.g. so that the next scanned plane is 1 mm higher than the previous plane), and the scan-and-rotate process repeated. When the scanning is complete, a three-dimensional image is reconstructed after the data is subjected to filtration and back-projection algorithms. While this scanner has successfully evaluated several dosimeters, it suffers from a number of drawbacks which limit its usefulness. Transmission data requires correction to account for deviation of the laser beam from a normal incidence angle. The angle of incidence of the laser beam upon the surface of the tank was adjusted to 5 degrees from the window normal to reduce multiple reflections. The stepper-driven lateral mirror translation apparatus is vulnerable to error (precision motion of a relatively large structure is needed), resulting in a potential loss of resolution. The axial translation of the dosimeter required to measure slices perpendicular to the dosimeter axis represents another source of error. It is necessary to carefully align the center of the scan length with the axis of rotation of the dosimeter. The scanned area of each slice must be restricted to 90% of the diameter of the dosimeter. Errors in beam wandering across the face of the detector need to be compensated by the addition of a diffusing window and a converging lens. The most objectionable feature of this scanner is its long acquisition time. The total data acquisition time for a 60×60 pixel image was six minutes. Imaging of another object required approximately 2 seconds per profile, leading to an imaging time of about 12 minutes per slice. Total acquisition time for dosimeters of clinically relevant volume can exceed eighteen hours. True three-dimensional scans, with isotropic high resolution and a large field-of-view in the slice direction are not feasible using this methodology, particularly on a routine clinical basis.

Optical CT scanners employing area detectors have been developed. Scanners with CCD or CMOS area detectors have become feasible with the widespread availability of high-quality digital cameras. Whereas laser systems acquire data in a point-by-point fashion, imaging area detectors allow the acquisition of a complete two-dimensional projection at once. Each two-dimensional projection gives the data required for creating a row in the sinogram for every slice in a three-dimensional reconstruction. Currently scientific CCD cameras have a typical matrix size of 1000×1000 pixels, so improvements of over two orders of magnitude in acquisition time over the Gore et al instrument (U.S. Pat. No. 6,218,673, vide supra) are theoretically possible. In practice, the speed when using a CCD-based system is often limited by the data-throughput rate, in particular the rate at which the data may be transferred out of the camera to the host computer. A disadvantage of the CCD system is its sensitivity to various types of artifacts. As opposed to the point illumination achievable with laser optical CT scanning, brightfield illumination utilized with CCD-based optical CT scanners can give rise to increased noise due to light scattering, stray light detection and, most significantly, differential refraction of incident light by regions of the sample with subtly different refractive indices (schlieren artefacts).

An optical CT scanner with a CCD area detector was disclosed (Bero, M. et al, 1999, DOSGEL 1999, 1st International Workshop on Radiation Therapy Gel Dosimetry, Kentucky). This scanner, based on parallel-beam geometry, utilized a LED light source with a lens arrangement to deliver parallel beams through a dosimeter immersed in refractive-index matching liquid. The dosimeter was rotated through a small discrete angle between the acquisitions of two-dimensional slices. The data was treated with filtration and back-projection algorithms and was reconstructed into a three-dimensional image.

A similar optical CT scanner employing cone-beam geometry was introduced (Wolodzko, J. et al, 1999, *Medical Physics*, 26(11), 2508-2513), developed (Jordan, K. et al, 2001 *DOSGEL 2001, Second International Conference on Radiotherapy Gel Dosimetry*, Brisbane, 2001) and commercialized (Modus Medical Devices Inc., London, ON).

Recently optical CT scanners with laser light sources and improved acquisition times have been developed. The decrease in time required to scan an object relative to the Gore et al instrument (U.S. Pat. No. 6,218,673, vide supra) was achieved by adopting rotating mirrors to guide scanning in a raster fashion.

A scanner employing a single rotating mirror to scan laser light through a cylindrical sample was disclosed (Maryanski et al, 2001, *Proc. SPIE*, 4320, 764-774). This scanner was used for three-dimensional mapping of optical attenuation coefficient within translucent cylindrical objects. The scanner design utilized the cylindrical geometry of the imaged object to obtain the desired paths of the scanning light rays. A rotating mirror and a photodetector were placed at two opposite foci of the translucent cylinder that acts as a cylindrical lens. A laser beam passed first through a focusing lens and then was reflected by the rotating mirror, so as to scan the interior of the cylinder with focused and parallel paraxial rays that were subsequently collected by the photodetector to produce the projection data, as the cylinder rotates in small angle increments between projections. Filtered backprojection was then used to reconstruct planar distributions of optical attenuation coefficient in the cylinder. Multi-planar scans are used to obtain a complete three-dimensional tomographic reconstruction. The scanner was designed for use in radiation therapy dosimetry and quality assurance for mapping three-dimensional radiation dose distributions in various types of tissue-equivalent gel phantoms that change their optical attenuation coefficients in proportion to the absorbed radiation dose. This scanning system, in part due to the reliance upon the cylindrical shape of the gel dosimeter to function as a lens in the optical path, is able to scan only a fraction of the volume contained within the dosimeter, thereby limiting its usefulness. Moreover, the scanner uses only a single mirror, leading to deflection of the laser beam in only one dimension. Thus, to image multiple slices, the sample must again be translated axially, as for the original scanner of Gore et al (U.S. Pat. No. 6,218,673 vide supra). Motion of the mirror is uni-direction, rather than back and forth. This means that for a significant fraction of each cycle ~⅚, no useful data is being acquired. This limits the utility of the scanner.

An optical CT laser scanner employing a single rotating plane mirror has been described (van Doorn, T. et al, 2005, *Australasian Physical Engineering Sciences in Medicine*, 28, 76-85). In this scanner, laser light reflects from the rotating mirror and is directed to either a stationary plane mirror or to a first converging lens. When the light is directed to the stationary mirror, it is reflected into the detector for reference measurement. When the light beam is reflected from the rotating mirror into the acceptance aperture of the first lens, it is refracted to pass through an object immersed in a refractive index matching bath. The rotating mirror, mounted at the focal point of the first lens, directs the laser beam to scan a plane through the object, forming a set of parallel rays. A second converging lens refracts the light into the detector. Although the scanner was designed to have the capacity to form $1.0$ mm$^3$ voxels over the volume of a cylinder with a diameter of 100 mm and a height of 70 mm, the authors report a single reconstructed plane image produced from incremental stepped revolution of the object in 1.25 degree intervals, mirror rotation speed of 120 revolutions per second, and a total scan speed (one slice) of 2.4 seconds. Presumably the device will need to be altered to permit sampling of the entire volume of the object. This might be accomplished by advancing the object axially to scan consecutive planes through the object perpendicular to the object axis. Because the mirror rotates, it is inefficient in data acquisition in the same way as the scanner of Maryanski (vide supra).

An optical CT scanner comprised of a laser light source, a single rotating mirror, a lens pair, and a tilting yoke was disclosed (Conklin, J. et al, 2006, *Journal of Physics Conference Series* 56, 211-213). Two aspherical Fresnel lenses (200 mm focal length, 254 mm diameter, 8 grooves per mm) were placed on either side of an aquarium containing water into which the object to be scanned was placed. Two thin front surfaced mirrors were attached back to back to a steel cylinder attached directly to a small DC motor shaft. The rotating mirror assembly was mounted on a U shaped yoke that allowed the mirrors to tilt as well. The mirror assembly was positioned at the focal point of the input Fresnel lens. Stepper motors control mirror tilt and sample rotation. The tilting of the yoke allowed scanning of planes orthogonal to the axis of the dosimeter. Vertical beam stops at the aquarium edges provided start and stop reference positions. The photodiode detector was placed at the focal point of the exit Fresnel lens. The mirror rotated continuously at 10 Hz. The scanner algorithm involved recording a specified number of points after the signal exceeded a specified threshold followed by a mirror tilt. This sequence was repeated from top to bottom of the sample forming a raster scan. Next the sample was rotated and the raster scan was again repeated. Typical scan values: 1200 points per 150 mm, 200 projections per 180 degrees and 25 minutes per 75 slices. The samples were aqueous patent blue violet solutions and the cylinders were PFA Teflon tubes 96 mm OD and 0.5 mm wall thickness. Profile data points were converted from time to position by assuming a constant mirror rotation frequency and measuring the distance between the start and stop beam stops located at the aquarium edges. Poor resolution due to the use of Fresnel lenses and variability in motion control of the rotating mirror and tilting yoke limits the usefulness of this technique.

The present invention shares some optical attributes currently utilized in Confocal Microscopy and related techniques, which rely on excitation of a selected region of a fluorescent-labeled specimen by an incident beam of a first wavelength and detection of the emitted light of a second wavelength. U.S. Pat. No. 4,997,242 to Amos, W. describes Confocal Microscopy utilizing an optical assembly composed of two rotating plane mirrors, five stationary plane mirrors, two beam splitters and two stationary paraboloidal mirrors. An incident laser light beam is directed by the mirror-beam splitter assembly to a specimen. The mechanical working of the rotating mirrors allows the light beam to scan the sample in a raster pattern. The sample has been previously treated so that the interaction with the incident beam causes fluorescence to take place. With this technique, the depth of penetration of incident light is limited by the characteristics of the sample (usually a biological specimen) and the fluorescence is measured at 360 degrees to the incident beam. The emitted light from the fluorescing sample follows the same optical path as the incident beam, though in the opposite direction, and is diverted by mirrors and beam splitters into two photomultipliers. The function of the scanning assembly is to provide a raster scan of the specimen, into which the light penetrates a short distance, usually a maximum of a few hundred microns, to facilitate the emission of light having a wavelength different from the excitation wavelength. Recent improvements in confocal microscopy include two-photon and multi-photon techniques (Potter, S. et al, 1996, *Scanning*, 18, 147.) In a related technique, Selective Plane Illumination Microscopy, (Huisken, J. et al, 2004, *Science*, 305, 1007), a thin sheet of light is made to pass through a specimen at the focal plane of a microscope detecting orthogonal to the incident light plane. The sample has been previously treated so that the interaction with the incident beam causes fluorescence to take place. The emitted light is captured by the microscope's detector with little out-of-focus fluorescence detected. The result is data representing a "slice" of the specimen. The selected plane of incident light and the microscope focal plane are then adjusted to measure subsequent slices through the specimen. This technique allows the reconstructing a 3-D image from a set of 2-D projections at different sample rotations, using a reconstruction technique such as filtered back-projection. This technology is a variant of optical sectioning, which is well known in the art, and in which out-of-focus interference can be removed by computer deconvolution of a digitized image. This is an iterative computational technique in which a stack of focal sections is recorded and the contribution of out-of-focus signal to a given section from structures in other sections is computed and subtracted from that section. This has proved to be a powerful technique where the out-of-focus signal rejection required is not too great. However, it requires that a high level of registration is maintained as a focal series is being recorded.

A variant of optical CT currently employed is optical projection tomography (OPT), in which incident light travels through the object and is detected as a projection. Objects studied by this technique may be small, wherein the optical assembly might include a microscope component, or large, wherein magnification may not be desirable.

An OPT microscope transmits beams of light through a specimen at different angles. Projections of the specimen are recorded at the different angles. The projections are processed using tomographic computations to reconstruct the spatial distribution of the linear attenuation coefficient within the specimen. A series of projection slices are reconstructed to form a three-dimensional image of the object. Each element in each recorded projection corresponds to a line integral of the attenuation coefficient along the beam path. The line integral represents a total attenuation of the beam as it goes along a straight line through the specimen. A three-dimensional distribution of the attenuation coefficient provides information about the three-dimensional structure of the specimen. The projection data must be mathematically treated to allow the rendering of an accurate three-dimensional image. Algorithms to perform such treatment of data are well known (Kak, A. et al, 1988, *Principles of Computerized Tomographic Imaging*, IEEE Press) and improvements have been recently reported (see, inter alia, Walls, J. et al, 2005, *Phys. Med. Biol.* 50(19), 4645-65 and Wang, Y. et al, 2006, *Phys. Med. Biol.* 51(23), 6023-32). Objects imaged by detection of projections vary in size, depending upon the optical property measured and the ability of the object to transmit the incident light. Biological tissue samples, in which transmission is hampered by absorption and scattering, which are examined by OPT microscopy may be on the order of 1 $cm^3$. Transparent objects imaged by corresponding macro optical techniques might be as large as a cylinder with a radius of 8 cm and a height of 16 cm.

Optical Projection Tomography Microscopy was disclosed (Sharpe et al, 2002, *Science* 296, 541; WO/2002/0996; WO/2002/0997). In this technique, light is transmitted through a specimen and is detected by either a one-dimensional or two-dimensional array of detectors (e.g. charge-coupled device or CCD). The data is then filtered and treated with a back-projection algorithm to achieve a three-dimensional image. The specimen is immersed in an index-matching liquid to reduce the scattering of light. This means that light passes through the specimen in approximately straight lines and a standard backprojection algorithm can generate relatively high-resolution images. Inside the OPT scanning device, the specimen is maintained within the liquid, rotated to a series of angular positions (usually less than 1 degree apart), and an image is captured at each orientation. The apparatus is carefully aligned to ensure that the axis of rotation is perpendicular to the optical axis so that projection data pertaining to each plane is collected by a linear row of pixels on the charge-coupled device (CCD) of the camera. Light is shone into the back of the specimen, directly toward the objective lens, and the image formed records the attenuation of this beam. However, in reality, even specimens maintained in an index-matching liquid still cause diffraction, refraction, and scattering of photons as they pass through. The lenses act as collimators, so only rays that emerge from the specimen at specific positions and angles are sampled. In this invention, the optimal lamp for OPT is not a point source, but a wide-field illumination that, owing to the intrinsic scattering within the specimen, can in fact be a diffuse source. The technique can be used to image fluorescent-labeled samples.

A three-dimensional optical CT microscope employing a mirror with two axes of rotation was described (Chamgoulov, R. et al, 2005, Proc. SPIE 5701, 24-43; Chamgoulov, R. et al, WO/2006/03722, US2007258122). This system consists of two high numerical-aperture lenses, an optical scanner, a light source, and a light detector. A two-axis mirror equipped with motorized linear actuators serves as the optical scanner. In this invention, highly collimated light was passed through a beam expander and made to focus at the pupil plane of condenser lens by the assembly of a two-axis plane mirror and a scan lens. Incident light is thus made to pass through the sample in parallel lines. The angle of incidence $\phi$ of illumination upon the sample is varied within the acceptance aperture of the lens assembly ($0<\phi<135$ degrees), so that series of projections are made at varying angles through the sample. Light transmitted through the sample is refracted by an objective lens and recorded by a suitable light detector. New reconstruction algorithms containing feedback and error correction were needed to address the limited-angle reconstruction problem. The effects of these corrections on quantitative data remain to be tested, but it can be anticipated that unacceptable artifacts would occur for applications in which accuracy of order 1% is required, such as 3-D radiation dosimetry. This scanner is explicitly limited to microscopic imaging. This scanner is not a telecentric system, which is an important feature in metrological applications.

There remains an unmet need for an optical CT scanner capable of providing fast, reliable, and accurate three-dimensional images of macroscopic objects, such as those used in 3-D radiation dosimetry. The present invention provides an optical CT scanner which utilizes a novel arrangement of optical, mechanical, and electronic components to provide a rapid and precise raster scan of three-dimensional objects, leading to a set of two-dimensional projections, which can be processed to reconstruct high-resolution three-dimensional reconstructed images. The invention further provides means to achieve highly accurate and precise (i.e., with high signal-to-noise ratio) three-dimensional images in which unwanted optical artifacts, such as noise from stray light and scattering, are minimized.

BRIEF SUMMARY OF THE INVENTION

The invention relates to an optical scanning system in which a highly collimated light beam or laser light beam is made to form a series of two-dimensional projections by scanning a transmitting object in a two-dimensional raster pattern, changing the orientation of the object with respect to the scanning beam, and repeating the scanning and changing of orientation a plurality of times. Computerized algorithms are employed to filter and calculate back-projection images from the series of projections, and then a three-dimensional image is reconstructed using computerized tomographic techniques. The invention utilizes an optical scanning system comprised of two independently rotating plane mirrors. According to the invention, the mirrors rotate under computer control, wherein the precise position of the reflecting surface of each mirror is specified by software which causes appropriate signals sent to galvanometers controlling the rotation of the mirrors. The result is a precise two-dimensional raster scan of the object. Such precise computer control of two rotating plane galvanometric mirrors is an improvement over scanners incorporating a single continuously rotating mirror (vide supra). In one embodiment, the invention utilizes an optical system comprised of two independently rotating galvanometer plane mirrors and relay optics. Relay optics is defined herein a means to provide an optical path for a light beam deflected by the reflective surface of one rotating mirror to the reflective surface of the other rotating mirror. One non-limiting example of relay optics is a pair of stationary paraboloidal mirrors so positioned as to cause a light beam deflected by one rotating mirror to strike the second rotating mirror. A second non-limiting example of relay optics is a pair of stationary spherical mirrors so positioned as to cause a light beam deflected by one rotating mirror to strike the second rotating mirror. A third non-limiting example is a pair of lenses. The examples involving mirrors have the advantage of being an achromatic system. The invention provides for a means to change the plane of incidence of the scanning beam, for example by rotation of the object on an axis parallel to the scanning plane.

It is an object of the invention to provide a fast optical CT scanning system capable of providing high resolution three-dimensional images of optical data contained within translucent or transparent objects ranging in size from a sample having a volume of about 1 mm$^3$ to a cylinder having a radius of about 25 cm and a height of about 25 cm.

It is a further object of the invention to provide a fast optical CT scanning system capable of providing high resolution three-dimensional images of optical data contained in samples wherein the optical data comprises absorption, scattering, fluorescence, refractive index changes, or combinations of these.

It is a further object of the invention to provide a fast optical CT scanning system capable of providing high resolution three-dimensional images of optical data contained in irradiated three-dimensional dosimeters for the purpose of commissioning or providing Quality Assurance data for instruments designed to deliver radiotherapy for human patients, or for the evaluation, comparison, or modification of treatment plans for radiotherapy for human patients.

It is a further object of the invention to provide a fast optical CT scanning system to validate the delivery of simple or complex radiation fields to non-human subjects, for the purposes of therapy or other testing, or to any other radiation-sensitive material.

It is a further object of the invention to provide a fast optical CT scanning system capable of performing optical CT microscopy.

DETAILED DESCRIPTION OF THE INVENTION

Figure 1:
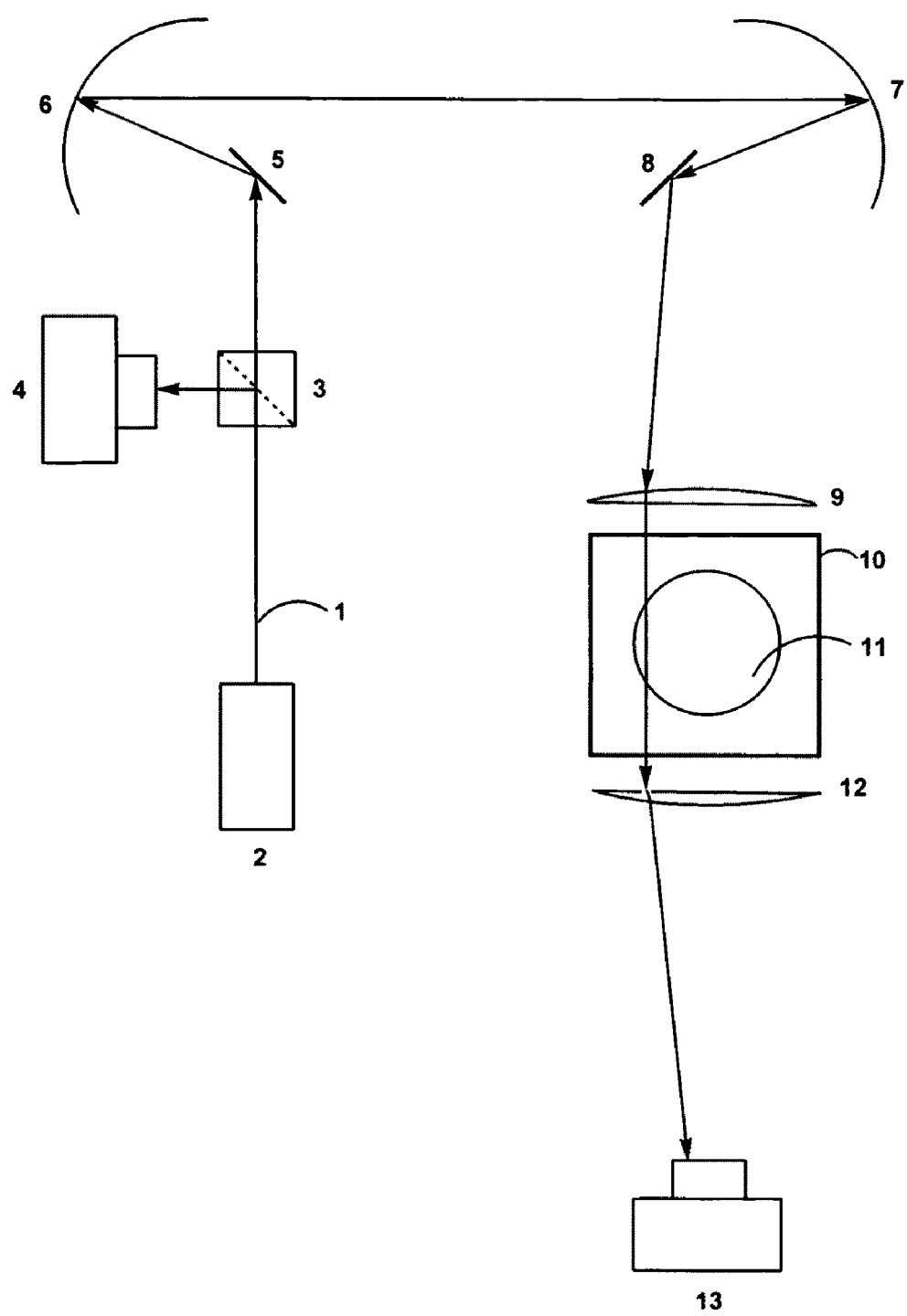
FIG. 1 represents schematically an example of a scanner of the invention. The light path is made to scan an object in two orthogonal directions (of which only one is shown in the figure), providing a planar projection, by reflection from two rotating plane mirrors. In this example the object is an irradiated dosimeter, which is made to rotate about an axis perpendicular to the plane of the figure.

The invention provides for efficient and high-resolution imaging of three-dimensional light-transmitting objects through the use of high-quality optics and a combination of precision motion control and precise alignment of carefully selected optical elements. According to the invention, galvanometer controlled rotating plane mirrors and stationary converging lenses, either with or without relay optics (consisting of, for example, a pair of paraboloidal or spherical mirrors), or using a commercially available laser "scan head", provide a means to scan an object along two axes. The net result of the optical arrangement is that a laser- or collimated light beam executes a two-dimensional scan across the sample in directions perpendicular to its direction of propagation. One embodiment provides a Cartesian raster scan suitable for three-dimensional image reconstruction using parallel-beam back-projection techniques. Alternative embodiments include, but are not limited to, devices providing a fan or cone-shaped raster scan, whose individual beams are transmitted through the sample in a well-controlled trajectory, resulting in projections suitable for reconstruction by alternative algorithms. Each complete scan provides a one- or two-dimensional projection image, depending on whether a single- or multiple-slice image is desired after reconstruction. The invention provides means to accumulate a plurality of these projection images in computer memory or appropriate storage. One way in which to glean optical information contained within a light-transmitting object according to the invention is to rotate the object about an axis parallel to the scanned plane in between successive scans. A second way is to arrange for the light paths to pass through the sample at different angles. Selection of the appropriate stepped rotation angle (for example 1.5 degrees) and the total rotation arc (for example 180 degrees) defines the number of planar raster scans required (120 scans in this example). Higher resolution images may be obtained by using a smaller stepped rotation angle (for example 0.5 degree). It is well known that projection data must be mathematically transformed before a tomographic reconstruction. These transformations might include the use of algorithms to accomplish filtering and back-projection. The algorithms accomplishing such transformations and tomographic reconstructions are well known in the art. Objects of various sizes may be imaged according to the invention. In one embodiment of the invention, an essentially cylindrical solid of radius about 25 cm and height of about 25 cm might be imaged. Such latter embodiment provides a means to produce high resolution, accurate, and precise three-dimensional images from dosimeters currently used in assessing radiotherapeutic parameters.

The present invention is an improvement over scanners previously described. The choice of optical and mechanical components allows a scanning method which is at once rapid and accurate and which provides reconstructed three-dimensional images with a high degree of resolution and precision. An example of an embodiment of the invention designed to scan cylindrical dosimeters is depicted schematically in FIG. 1. Light path 1 emanates from a helium-neon laser 2 (25-LHP-121-230, 2 mW, 0.59 mm beam width, red, 633 nm, Melles Griot, CA, USA) and is directed to beamsplitter 3 with split ratio 50/50 (CM1-BS1, Thorlabs, NJ, USA). The deflected beam is read out by a large area photoreceiver 4 (8 mm diameter, model 2031, New Focus, CA., USA) and provides a light field value which is necessary for attenuation measurements. The beam continues into the relay optics which consists of two galvanometer plane and two off-axis paraboloidal mirrors. The beam strikes galvanometer-controlled rotating plane mirror 5 (QuantumScan5, Nuffield Technology Inc, NH, USA) at a point of incidence carefully adjusted to be at the focal point of paraboloidal mirror 6 (02 POA 017, Melles Griot, CA, USA). The beam is then reflected into paraboloidal mirror 7 (02 POA 017, Melles Griot, CA, USA), which deflects the beam to a point of incidence on rotating plane mirror 8 (QuantumScan5, Nuffield Technology Inc, NH, USA). The point of incidence on 8 is carefully adjusted to be at the focal point of mirror 7. This point of incidence on 8 is also carefully adjusted to be at the focal point of large lens 9 (01-LPX-336, plano-convex, 440 mm focal length, 145 mm diameter, Melles Griot, CA, USA). Thus the beam exiting 9 is parallel to the optical axis. Varying the angle at which the beam leaves the focal point on mirror 8 is equivalent to scanning the beam exiting lens 9 in a rectangular raster fashion across the sample, such that the beam is always perpendicular to the face of the scanning tank 10. The light beam leaving 9 is parallel to the optical axis, and travels through scanning tank 10 containing refractive index matching medium and dosimeter 11, and is focused by lens 12 (Optical Surfaces, Kenley, UK, plano-convex, custom design, 500 mm focal length) into photoreceiver 13 (8 mm diameter, model 2031, New Focus, CA, USA) which measures the attenuated laser beam irradiance. A prototype apparatus measured 2 m long, 0.3 m high and 0.3 m wide. The length is determined largely by the focal lengths of lenses 9 and 10. It will be appreciated that the overall footprint of devices of the invention can be varied by selection of the focal length of paraboloidal mirror 6, paraboloidal mirror 7, lens 9, and lens 10. The impact of such focal lengths upon the dimensions of a device of the invention is well known in the art. The selection of such focal lengths may vary with the particular embodiment of the invention.

Figure 2:
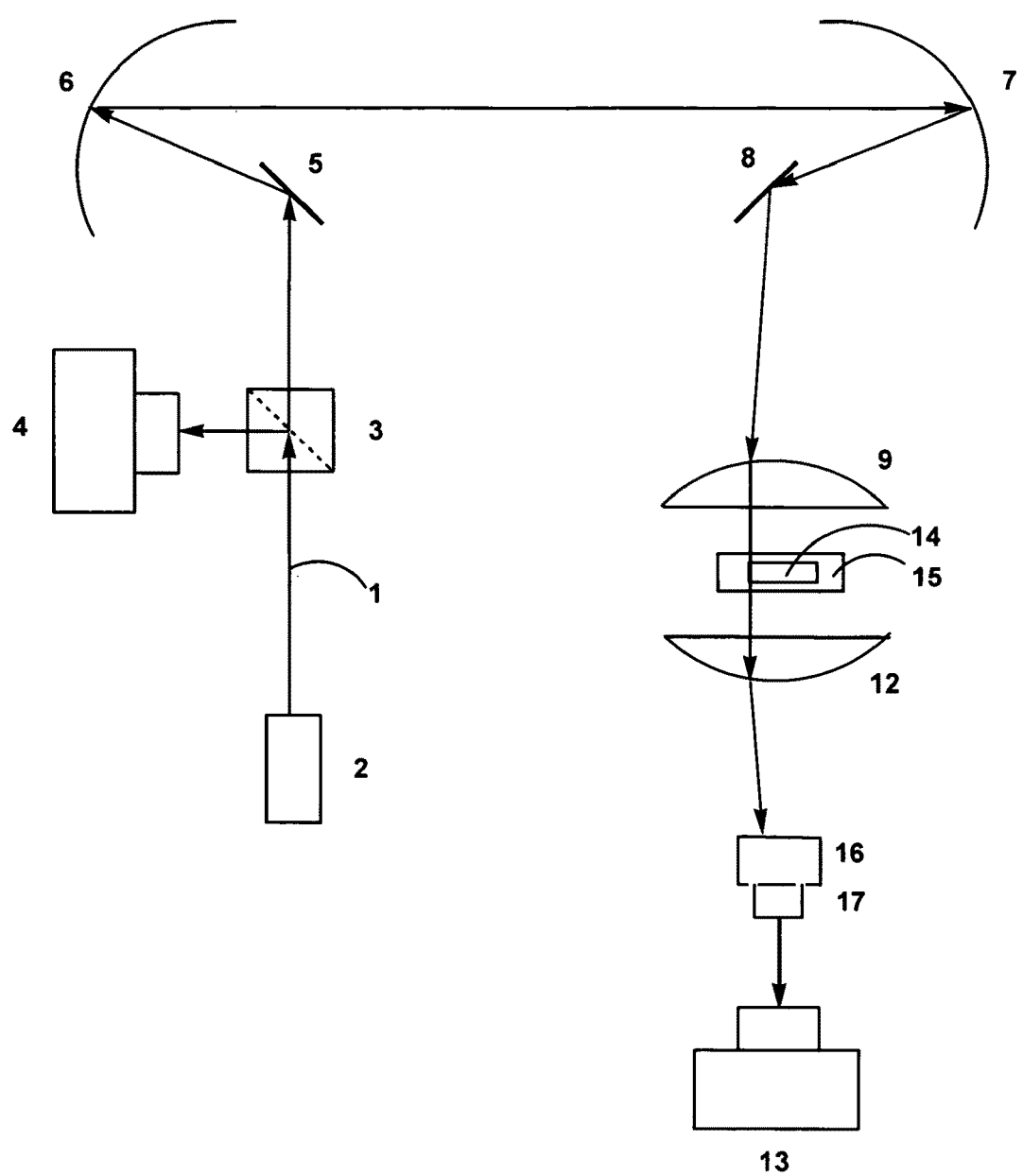
FIG. 2 represents schematically a second example of a scanner of the invention. The light path is made to scan an object in two orthogonal directions, providing a planar projection, by reflection from two rotating plane mirrors. In this example the components of the invention are arrayed to perform optical projection microscopy on a suitably prepared specimen.

FIG. 2 schematically depicts a second example of an embodiment of the invention designed to scan small transmitting samples such as, for a non-limiting example, tissue sections. The optics is similar to those of FIG. 1, except that the beam exiting condenser lens 9 pass through a sample 14 mounted on a stage 15. Stage 15 may be used to orient sample 14. Such orientation includes, but is not limited to, translation of 15 in a plane orthogonal to the plane of the raster scan, translation of 15 in a plane perpendicular to the plane of the raster scan, rotation of 15 in a plane orthogonal to the plane of the raster scan, and rotation of 15 about an axis parallel to the plane of the raster scan. Stage 15 may be so engineered as to provide means to immerse 14 in refractive index matching media. The beam exiting objective lens 12 is focused into optional additional optical elements 16 and 17. Elements 16 and 17 may function to further manipulate the beam before it enters photoreceiver 13. Such manipulation might include, but is not limited to, magnification, polarization, chromatic filtration, bandpass filtration, and photomultiplication, and combinations of these.

The operation of embodiments represented in FIGS. 1 and 2 is similar. In the embodiment of FIG. 1, an irradiated dosimeter is placed into the scanning tank. The laser beam is scanned in a square raster across the front face of the tank. The intensity of the laser beam reaching Photodetector 13 is recorded. The signal is synchronised with the position of the laser beam in such a way that it can be recorded in the form of a rectangular matrix. Appropriate computer software may be used as necessary to modify the control signals sent to the galvanometer in such a way as to correct (adaptively, if necessary) for any inaccuracies of optical alignment or limitations in the mechanical response of the galvanometers to their input signals. Furthermore, if necessary, various numerical post-processing algorithms may be used to correct any residual optical distortions present in the data matrix. This matrix corresponds to the raw projection data that are used to recreate the image by the process of filtered back-projection. The sample sits on a turntable. The rotation angle of the turntable is incremented and the raster scan of the laser is repeated to create a second 2-D data matrix. The whole process is repeated until a predefined number of projections have been acquired. These data are now sufficient to reconstruct a 3-D map of optical density, which is the desired outcome of the measurement.

Figure 3:
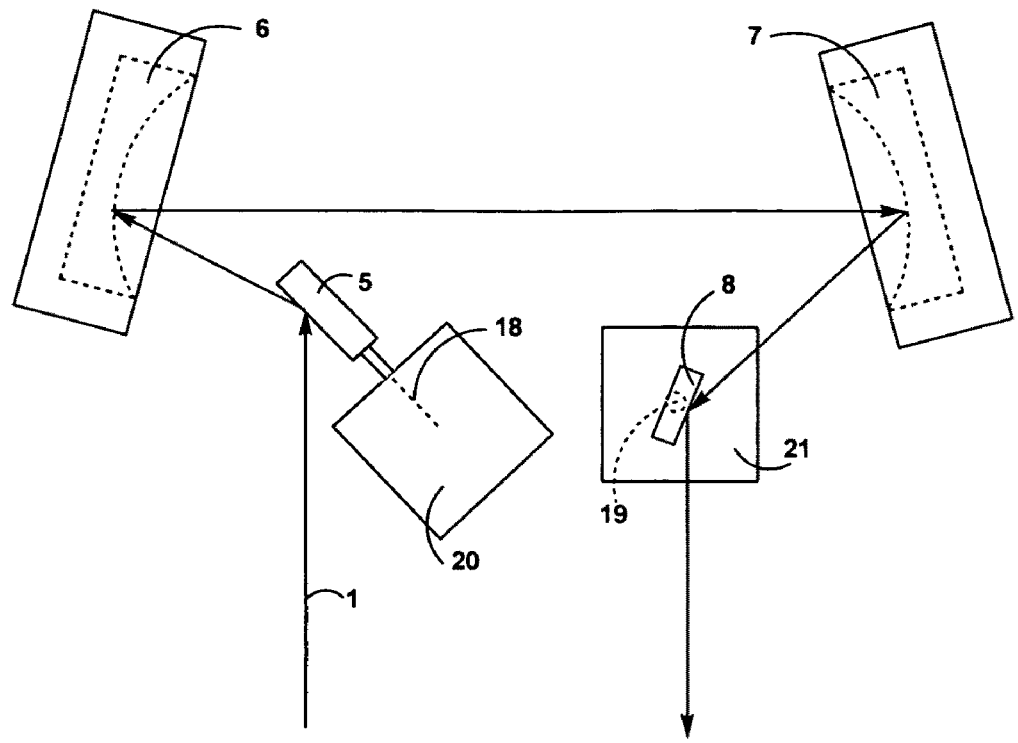
FIG. 3 illustrates an embodiment of the assembly of the optical components of the invention. The light beam is reflected from two orthogonally disposed rotating mirrors and an arrangement of two paraboloidal mirrors.

FIG. 3 schematically shows the relay optics assembly of one embodiment of the invention. Incident light beam 1, after leaving beamsplitter 3 (not shown, see FIG. 1) is deflected in turn by plane mirror 5, paraboloidal mirror 6, paraboloidal mirror 7, and plane mirror 8. Galvanometer drive 20 (QuantumDrive5000, Nuffield Technology Inc, NH, USA) provides precisely controlled rotation to plane mirror 5 about its axis 18. Axis 18 is in the plane of FIG. 3, and the reflective face of mirror 5 moves in and out of the plane of FIG. 3 upon rotation. Galvanometer drive 21 (QuantumDrive5000, Nuffield Technology Inc, NH, USA) provides precisely controlled rotation to plane mirror 8 about its axis 19. Axis 19 is orthogonal to the plane of FIG. 3, and the reflective face of mirror 8 moves in planes orthogonal to the plane of FIG. 3 upon rotation.

Figure 4:
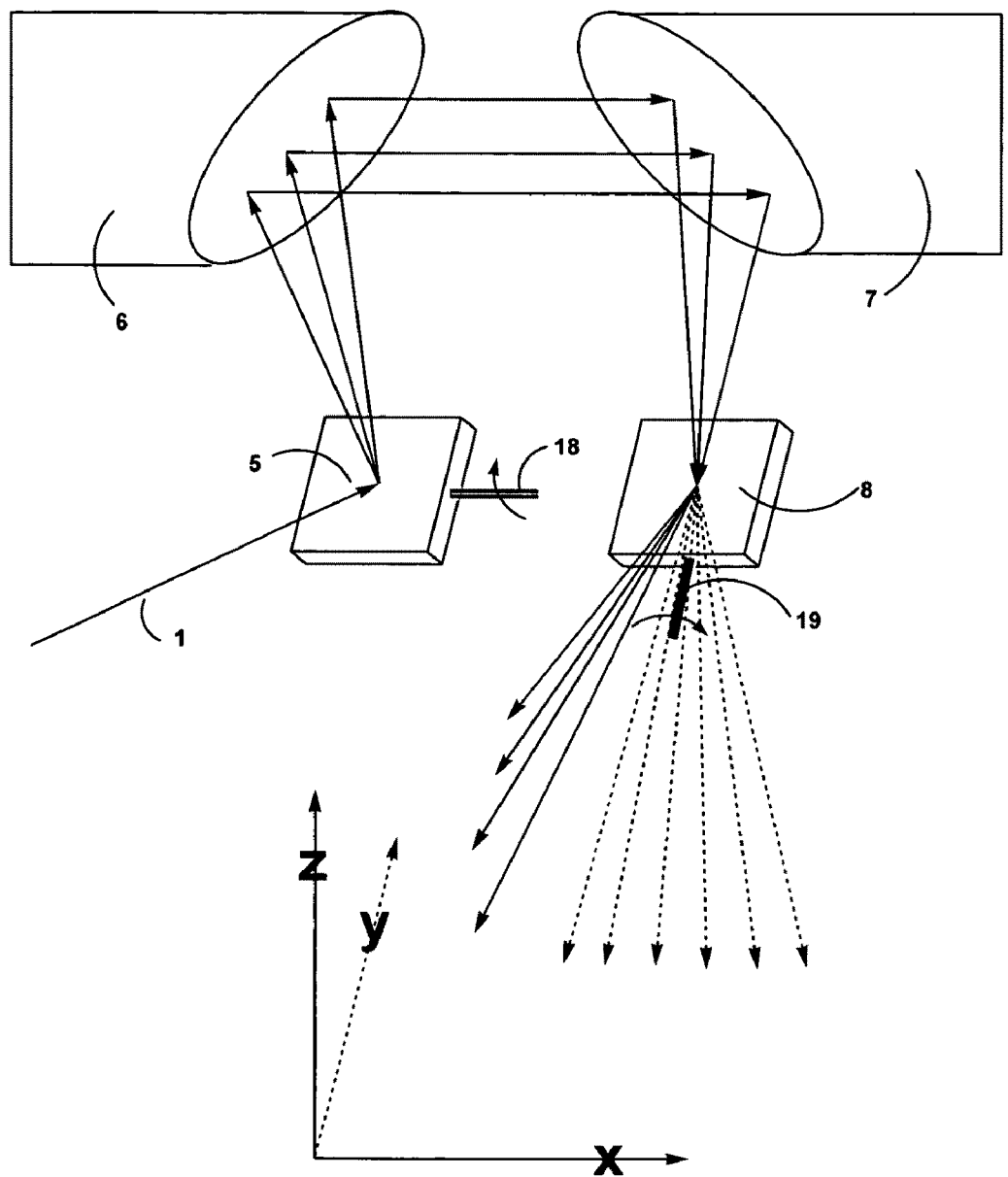
FIG. 4 illustrates an embodiment of the assembly of the optical components of the invention. The incident light beam is made to scan along two axes to provide a planar raster pattern through the rotation of two planar lenses and relay optics.

As seen in the alternative schematic rendering of the relay optics assembly of the invention in FIG. 4, the incidence point of beam 1 upon the surface of mirror 5 is static, and rotation about axis 18 causes the deflected beam to sweep across the paraboloid face of mirror 6. Deflection of such a sweep from the paraboloid face of mirror 7 causes convergence of the beams at a static incidence point on mirror 8. Deflection from mirror 8 of beams scanned by the rotation of mirror 5 causes a raster scan (solid arrows) parallel to the y axis as drawn. Rotation of mirror 8 about axis 19 correspondingly causes a raster scan (broken arrows) parallel to the x axis. It will be appreciated that, in the relay optics of the invention, if mirror 5 is rotated and mirror 8 is held stationary, the object (FIGS. 1 and 2) will experience a one-dimensional raster scan parallel to the y axis. Likewise, if mirror 5 is held stationary and mirror 8 is rotated, the object will experience a one-dimensional raster scan parallel to the x axis. Controlled cooperative rotation of both mirror 5 and mirror 8 through the appropriate arcs will provide a two-dimensional raster scan projected through the x-y plane.

According to the invention, each planar raster scan detected by 13 is stored in the appropriate computer memory media (not shown). It is well known in the art how to assemble and configure the interface between photodetectors and computers. The tomography scan may be done in step-and-shoot manner, where each shot registers a complete 2-D frame. However, in another embodiment, asynchronous and continuous rotation of the sample would be possible, leading to much faster acquisition times for the 3-D tomography scan. Software was written to control the whole process by sending appropriate waveforms to galvanometer drive (Quantum Drive 5000, Nutfield Technology Inc, NH, USA) via data-acquisition card (NI-PCI-6221, National Instruments, Dallas, Tex., USA). In the embodiment of FIG. 1, dosimeter 11 is rotated between shots by a rotation stage (PRS-110, Micos Gmbh, Germany, not shown) which is stepper motor driven. In this embodiment, the rotation stage is placed above the optical glass cell 10 (700-062OG, Hellma Optik, Jena, Germany). Dosimeter 11 (PRESAGE™, Heuris Pharma, Skillman, N.J., USA) is attached to the rod linked to the rotation stage and immersed in refractive index matching liquid (mixture of diallyl-phthalate and dibutyl-phthalate) in the glass cell. Data is acquired synchronously from photoreceivers 4 and 13 (FIGS. 1 and 2) at 16 kHz frequency. Therefore, only the laser fluctuation within a 60 μs period affects the measurement.

It will be appreciated that in one embodiment of the invention depicted in FIG. 2, it may be desirable to record only one planar raster scan through 14 if, for one non-limiting example, the sample 14 is a thin tissue section. In such an embodiment data filtering and back-projection may be applied, but tomographic manipulation becomes unnecessary. It will be appreciated that in another embodiment of the invention depicted in FIG. 2, stage 15 may function as to impart a translation or rotation of sample 14 in a plane parallel to or orthogonal to the plane of the raster scan. In this embodiment, as that described in FIG. 1, the tomography scan could be done in either a step-and-shoot manner, where each shot registers a complete 2-D frame, or asynchronously, during continuous rotation of 15. The step in this embodiment would be an increment in translation or rotation of 15.

It will also be appreciated that the optical scanning system portrayed in FIGS. 3 and 4 might be provided by commercially available custom or purpose-built integrated scan heads, as are currently used in confocal microscopy, laser display, and entertainment (laser light shows). Such scan heads are available from, inter alia, Nuffield Technology, Windham, N.H. (http://www.nutfieldtech.com/nuffield/scan-heads.asp).

The present invention provides an improvement over the scanners currently in use or previously described. For optimal utility, a scanner should have the capability to perform a rapid scan of an object and provide an accurate, precise, and high-resolution three-dimensional image. Current scanners cannot deliver all of these parameters. Through extensive experimentation with various optical systems it was found that precise alignment and precise motion control of the optics of the invention gave results of unexpected resolution and precision. Due to the selection and arrangement of high-quality optical components, devices of the present invention are capable of precise planar raster scanning of objects in a large range of sizes, providing projection data of use in optical CT microscopy and in the scanning of large objects, with the result that high-resolution three-dimensional images are now possible in a short period of time. While the device disclosed in U.S. Pat. No. 6,218,673 to Gore et al (vide supra) required six minutes to scan a single-plane 60×60 pixel image, a device of the present invention is capable of obtaining a 60×60 pixel projection in under half a second. With a projection every one degree, as described earlier, a full 3-D dataset reconstructed as 60×60×60 cubic voxels could be acquired in under 2 minutes, thus leading to a data acquisition rate more than two orders of magnitude higher than the previously disclosed device.

Previously, an optical arrangement similar to that of the present invention offered the ability for light to penetrate specially treated specimens to a depth of only about one millimeter (U.S. Pat. No. 4,997,242 to Amos, W., vide supra). In this previous arrangement, several beamsplitters and mirrors attenuated the incident beam, and detection was allowed only for light with a wavelength substantially different than that of the incident beam. The technique allowed only the detection of fluorescence in the sample, and, due to the nature of fluorescence, the intensity of emitted beams was often low, thus requiring the incorporation of at least two photomultipliers to achieve effective detection. In addition, the path followed by the emitted beam was the same as the excitation path, but in the reverse direction, necessitating the addition of beamsplitters which consequently attenuated the signal. The present invention, in contrast, provides a simple optical arrangement wherein the optical path is altered by mirror rotation precisely controlled by computer-actuated galvanometers. Accordingly, the beam is attenuated only by interaction with the four mirrors, two lenses, the object, and whatever refractive index matching media is required. The optical system of the present invention is not limited to analysis of very small samples but is capable, in some embodiments, of measuring the optical properties of objects as large as a cylinder having a diameter of 25 cm and a height of 25 cm.

Rotating mirrors used to deflect laser light are well-known. They have been employed in various optical applications, including barcode readers, high-resolution display, dermal lesion ablation, geodetic scanning, and LIDAR (Light-Imaging Detection and Ranging). The incorporation of galvanometer-driven mirrors allows the combination of high speed and precise positioning of the laser beam. Galvanometer mirror parameters, such as moment of inertia, size of the mirror surface, and composition of the reflecting surface are carefully chosen for best performance for the particular embodiment of the invention. Paraboloidal mirrors are also well known, and have been utilized in several different optics application including reflecting telescopes, three-dimensional computer vision, radio astronomy, solar furnaces, and omni-directional cameras. Paraboloid mirror parameters, such as numerical aperture, focal length, and composition of the reflecting surface are carefully chosen for best performance for the particular embodiment of the invention. Converging lenses have had ubiquitous use in optical applications. The employment of such lenses to convert a diverging cone of laser light into a parallel raster is a standard technique. The employment of two independently rotating mirrors under precise computer control provides a significant improvement over current optical CT technology. In addition, the assembly of a pair of converging lenses, two galvanometric mirrors, and two paraboloidal or spherical mirrors in the manner of the embodiment of FIG. 1 represents a new and much improved arrangement for scanning three-dimensional objects. The need for improvements in the speed and resolution of the three-dimensional scanning process has been recognized since the description and use of the Gore et al scanner (U.S. Pat. No. 6,218,673 to Gore et al, vide supra) in 1996. The improvements disclosed herein represent the result of much research and many trials, and provide a scanner which satisfies the long-felt need for a rapid three-dimensional optical CT scanner.

Figure 5:
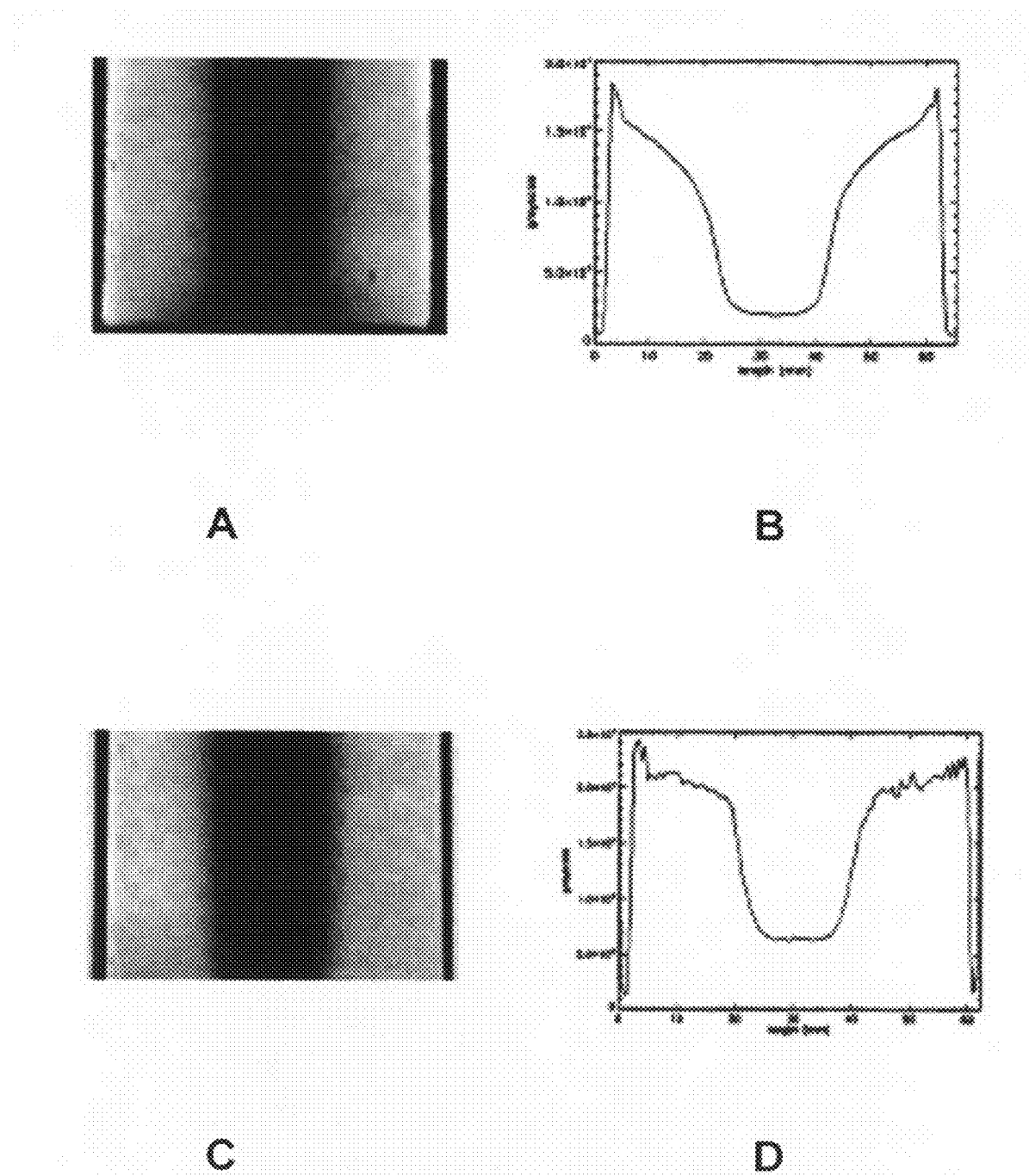
FIG. 5 compares projection data and line profiles of the projection data measured by a scanner of the invention and by a previously described CCD-based scanner.

Although scanners employing a diffuse light source and wide-array detection are able to capture a two-dimensional image rapidly, they suffer from optical artifacts which interfere with the resolution of the image. A device of the invention minimizes such artifacts. FIG. 5 shows a comparison of a projection taken with the current laser scanning apparatus and a projection taken previously using the CCD based apparatus (Krstajic et al, 2006, *DOSGEL* 2006, *Fourth international conference on radiotherapy gel dosimetry* (*Sherbrooke*) 123-125; Krstajic N et al, 2006, *Physics in Medicine and Biology* 51 2055-2075). FIG. 5A shows the line profile across a sample projection of a PRESAGE™ dosimeter obtained using the fast laser scanning apparatus (projection image matrix size 128×128, pixel size 0.5 mm×0.5 mm). FIG. 5B represents the corresponding line profile across a sample projection (128×128, pixel size 0.5 mm×0.5 mm) of a previous scan of the same sample in a CCD-based apparatus. The data obtained by the new laser scanner is superior both in terms of signal-to-noise ratio and level of artefact. The CCD scan is strongly influenced by schlieren, i.e., small inhomogeneities in refractive index, within the sample. These inhomogeneities in the scanned object and in the surrounding refractive index matching liquid lead to a greater level of image artefact when the whole volume of the dosimeter is illuminated, which is the case with CCD based optical-CT instruments. With laser based optical-CT only a thin line through the dosimeter is illuminated and detected, so only inhomogeneities along this line affect the end result.

Figure 6:
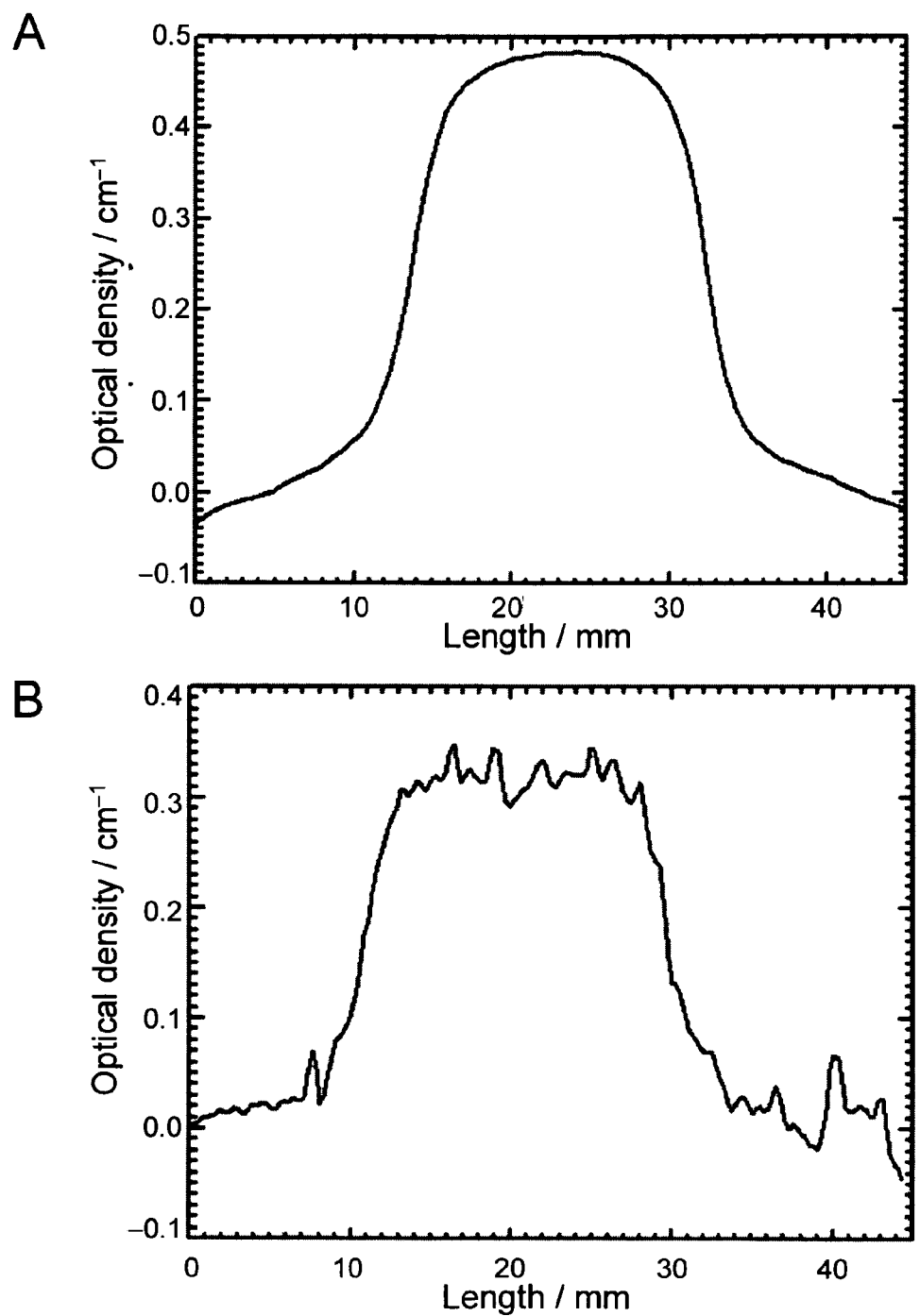
FIG. 6 compares reconstructed data and line profiles of the reconstructed data measured by a scanner of the invention and by a previously described CCD-based scanner.

The difference in image quality between CCD-based scanners and the laser optical CT scanner of the invention is further illustrated in FIG. 6. A profile across the reconstruction of a single slice of a PRESAGE™ dosimeter obtained using the fast laser scanning apparatus (128×128, voxel size $(0.5 \text{ mm})^3$) is shown in FIG. 6A. FIG. 6B shows a line profile across a reconstruction of a previous scan of the same sample in a CCD based apparatus (128×128, voxel size 0.5 mm). A slice with strong schlieren artifacts in the original CCD projection has deliberately been chosen. The line profile is significantly smoother with the fast laser scanning apparatus without compromising the spatial resolution.

Figure 7:
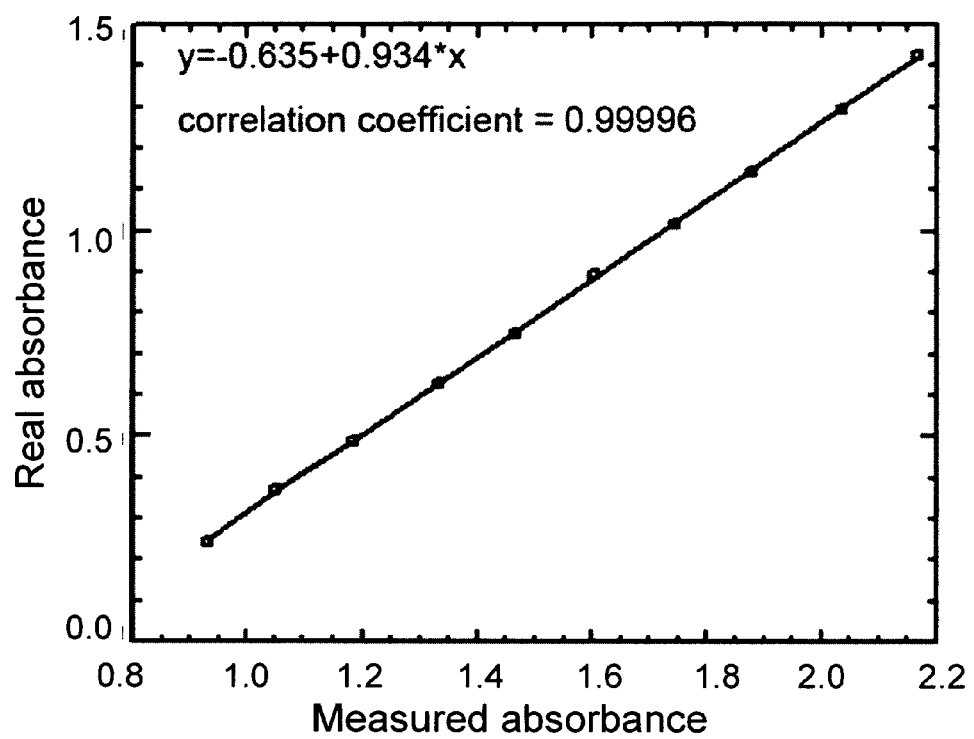
FIG. 7 illustrates the resolution and linearity of response of a scanner of the invention.

The linearity of absorbance measurements using the new laser scanner is shown in FIG. 7. Note that the measured absorbance range is 0.8 to 2.2 while the real absorbance range is 0.1 to 1.5. The offset in measured absorbance is due to additional attenuation of the beam in all optical surfaces (4 mirrors and 2 lenses) and the optical matching liquid. This discrepancy may easily be calibrated and corrected. The correlation coefficient in 7B is 0.99996 indicating that accuracy of absorbance measurements in this range is very high.

We claim:

1. A scanner for imaging optical properties of a three-dimensional object ranging in size from a volume of about 1 $cm^3$ to a cylinder having a radius of about 25 cm and a height of about 25 cm, said scanner comprised of:
   a highly collimated light source emitting a light beam transmitted through said object;
   a first photoreceiver, for measuring the attenuation of said light beam by said object;
   a first and second rotating mirror;
   a first converging lens;
   a tank containing refractive index matching liquid in which the object is immersed;
   a means to rotate said object about an axis substantially perpendicular to the optical axis;
   a computer for controlling the movement of said rotating mirrors, for controlling the orientation of the object with respect to the scanning beam, and for calculating said optical properties;
   wherein said imaging comprises forming a series of two-dimensional projections by scanning said object in a two-dimensional raster pattern, changing the orientation of the object with respect to the scanning beam, repeating the scanning and the orientation a plurality of times, employing computerized algorithms to filter the series of projections, and reconstructing a three-dimensional image using computerized tomographic techniques.

2. The scanner according to claim 1 further comprising relay optics.

3. The scanner according to claim 2 wherein the rotating mirrors are galvanometric mirrors.

4. The scanner according to claim 3 wherein said relay optics is selected from the group consisting of paraboloidal mirrors and spherical mirrors.

5. The scanner according to claim 3 wherein said relay optics is comprised of a first paraboloidal mirror and a second paraboloidal mirror.

6. The scanner according to claim 5 further comprising a beamsplitter, a second photoreceiver, and a second converging lens, wherein said light beam is split by said beamsplitter so that a first portion of the beam falls on said second photoreceiver allowing a reference intensity to be measured, and a second portion of the beam encounters the surface of said first rotating mirror, is deflected onto the surface of said first paraboloidal mirror, is subsequently deflected onto the surface of said second paraboloidal mirror, is subsequently deflected onto the surface of said second rotating mirror, is subsequently deflected through said first converging lens, is subsequently transmitted through said object, is subsequently passed through said second converging lens, and subsequently enters said first photoreceiver.

7. The scanner according to claim 6, wherein said light beam is split by said beamsplitter so that a first portion of the beam encounters the surface of said first rotating mirror, is deflected onto the surface of said first paraboloidal mirror, is subsequently deflected onto the surface of said second paraboloidal mirror, is subsequently deflected onto the surface of said second rotating mirror, is subsequently deflected through said first converging lens, is subsequently transmitted through said object, is subsequently passed through said second converging lens, and subsequently enters said first photoreceiver; and so that a second portion of the beam falls on said second photoreceiver allowing a reference intensity to be measured, such measurement is made to be stored in a computer memory, said object is rotated on an axis substantially perpendicular to the optical axis, the measurement and rotation are repeated a plurality of times, and a three-dimensional image is generated using computed tomographic means.

8. The scanner of claim 1 wherein said attenuation is absorption.

9. The scanner according to claim 1 in which said collimated light source is a laser.

10. The scanner according to claim 1 wherein the means to rotate causes an increment of 0.5 to 1.5 degrees.

11. The scanner of claim 10 wherein the means to rotate causes an increment of about one degree, and said image is 60×60×60 cubic voxels.

12. The scanner of claim 11 wherein the image is acquired in less than two minutes.

13. The scanner of claim 1 wherein the three-dimensional object is a dosimeter used in assessing radiotherapeutic parameters.

* * * * *